(12) United States Patent
Richter

(10) Patent No.: US 8,729,304 B2
(45) Date of Patent: May 20, 2014

(54) 1,4,2-DIAZAPHOSPHOLIDINE DERIVATIVES

(75) Inventor: Frank Richter, Leverkusen (DE)

(73) Assignee: Bayer MaterialScience AG (DE)

( * ) Notice: Subject to any disclaimer, the term of this patent is extended or adjusted under 35 U.S.C. 154(b) by 301 days.

(21) Appl. No.: 13/122,440

(22) PCT Filed: Sep. 24, 2009

(86) PCT No.: PCT/EP2009/006893
§ 371 (c)(1),
(2), (4) Date: Apr. 4, 2011

(87) PCT Pub. No.: WO2010/037499
PCT Pub. Date: Apr. 8, 2010

(65) Prior Publication Data
US 2011/0207927 A1    Aug. 25, 2011

(30) Foreign Application Priority Data
Oct. 4, 2008  (DE) .......................... 10 2008 050 414

(51) Int. Cl.
*C07F 9/6584* (2006.01)
*C07B 43/06* (2006.01)

(52) U.S. Cl.
USPC ............................................. 564/13; 568/12

(58) Field of Classification Search
USPC ............................................. 564/13; 568/12
See application file for complete search history.

(56) References Cited

U.S. PATENT DOCUMENTS

| | | |
|---|---|---|
| 3,551,527 A | 12/1970 | Weber et al. |
| 3,904,654 A | 9/1975 | Birum |
| 3,965,127 A | 6/1976 | Birum |
| 3,980,618 A | 9/1976 | Birum |
| 3,989,727 A | 11/1976 | Birum |
| 2011/0207927 A1* | 8/2011 | Richter .................... 544/223 |

OTHER PUBLICATIONS

Richter, "1,4,2-Diazaphospholidine-3,5-diones and Related Compounds: A Lecture on Unpredictability in Catalysis," *Chem. Eur. J.* (2009), vol. 15, pp. 5200-5202.

* cited by examiner

*Primary Examiner* — Venkataraman Balasubramanian
(74) *Attorney, Agent, or Firm* — Novak Druce Connolly Bove + Quigg LLP

(57) ABSTRACT

The present invention relates to a 1,4,2-diazaphospholidine of the formula (1)

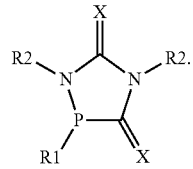

formula (1)

wherein

R1, R2 represent, independently of one another, saturated or mono- or polyunsaturated $C_1$-$C_{20}$-alkyl, -alkenyl, -alkynyl or $C_5$-$C_{40}$-aryl groups optionally substituted or interrupted by at least one heteroatom selected from the group consisting of N, O, S, and halogen, and X represents identical or different substituents selected from the group consisting of O, S, and N—R2.

8 Claims, No Drawings

1,4,2-DIAZAPHOSPHOLIDINE DERIVATIVES

CROSS REFERENCE TO RELATED APPLICATIONS

This application is a national stage application (under 35 U.S.C. §371) of PCT/EP2009/006893, filed Sep. 24, 2009, which claims benefit of German application 102008050414.9 filed Oct. 4, 2008.

BACKGROUND OF THE INVENTION

The present invention relates to novel 1,4,2-diazaphospholidine derivatives, to a process for preparation thereof and to use as catalysts.

Diazaphospholidines, especially species with a P—N—C—N—C sequence in the five-membered ring, are rare and generally occur in moderate yields in reactions which require reactants which are difficult to synthesize and are often associated with the formation of by-products which are either difficult to remove or can only be recycled with very great difficulty back into the production cycle of the reactant(s) (cf., for example, Zhurnal Obshchei. Khimii (1980) 50 (7), 1446-1451; Izv. Akad. Nauk, Ser. Khim. (1996) 7, 1857-1859; U.S. Pat. No. 3,551,527, U.S. Pat. No. 3,980,618, U.S. Pat. No. 3,989,727, U.S. Pat. No. 3,980,618, U.S. Pat. No. 3,965,127, U.S. Pat. No. 3,904,654).

Diazaphospholidines with geminal carbonyl groups and two P—N bonds in the ring are known from phosphorus and sulphur (1980) 8, 27-36.

1,4,2-Diazaphospholidine-3,5-diones, 1,4,2-diazaphospholidine-3,5-dithiones and the corresponding phosphacycles where R2-N=substituent(s) in place of one or both chalcogen atoms are entirely unknown.

2,5-Dihydro-1H-phospholes are often contaminated with the unsymmetrically substituted equivalents, the 2,3-dihydro-1H-phospholes. The latter are of interest as catalysts for isocyanate oligomerization, and so they first have to be freed of undesired constituents such as the 2,5-dihydro isomers before use in the oligomerization reaction.

BRIEF SUMMARY OF THE INVENTION

It has now been found that, very surprisingly, the reaction of the 2,5-dihydro-1H-phospholes (3-phospholenes, symmetric phospholenes) of the formula (2) with isocyanates R2-NCO (where X=O); isothiocyanates R2-NCS (where X=S) or carbodiimides R2-NCN—R2 (where X=NR2) leads virtually quantitatively in relation to the 3-phospholene to 1,4,2-diazaphospholidine structures of the formula (1).

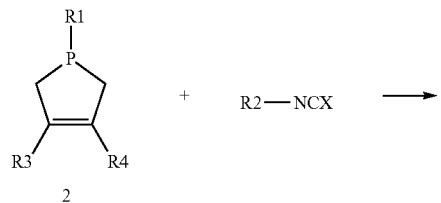

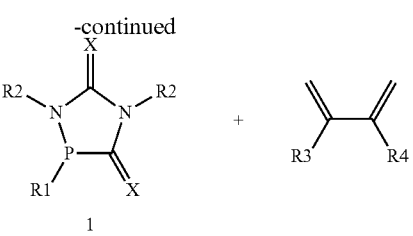

This procedure is suitable, for example, for removing 2,5-dihydro-1H-phospholes by derivatizing the 2,3 isomers which are of interest for the NCO oligomerization. Additionally of interest are compounds of the formula (1) for catalysis applications.

The present invention provides compounds of the formula (1) and a process for preparation thereof, and use as catalysts.

R1, R2 are each independently identical or different saturated or mono- or polyunsaturated $C_1$-$C_{20}$-alkyl, -alkenyl, -alkynyl or $C_5$-$C_{40}$-aryl groups optionally substituted or interrupted by heteroatoms (N, O, S, halogen).

X represents identical or different substituents from the group of O, S and N—R2, where X is preferably oxygen or sulphur.

R3, R4 are each independently identical or different substituents from the group of H, alkyl, aryl, preferably H and/or methyl.

In the process according to the invention for preparing the above-described 1,4,2-diazaphospholidine derivatives, 3-phospholenes of the formula (2) are reacted in a molar ratio of 1:2 to 1:100, preferably 1:2 to 1:5, with isocyanates R2-NCO, isothiocyanates R2-NCS or carbodiimides R2-N=C=N—R2.

DETAILED DESCRIPTION OF THE INVENTION

Suitable starting materials for the inventive reaction are in principle all linear or branched aliphatic, cycloaliphatic and aromatic mono-, di-, tri- and polyisocyanates, -isothiocyanates (mustard oils) and -carbodiimides. The latter can be generated advantageously in one step from the parent isocyanates.

Examples include: methyl iso(thio)cyanate, ethyl iso(thio)cyanate, allyl iso(thio)cyanate, all regio- and stereoisomers of the mono-, di-, tri- and polyiso(thio)cyanates mentioned hereinafter: propyl iso(thio)cyanates, butyl iso(thio)cyanates, hexyl iso(thio)cyanates, octyl iso(thio)cyanates, alkoxyalkyl iso(thio)cyanates, for example methoxypropyl iso(thio)cyanate, cyclohexyl iso(thio)cyanate, (methyl)cyclohexane diiso(thio)cyanates, ethylcyclohexane diiso(thio)cyanates, propylcyclohexane diiso(thio)cyanates, methyl diethyl cyclohexane diiso(thio)cyanates, phenyl iso(thio)cyanate, phenylene diiso(thio)cyanates, tolyl iso(thio)cyanates, tolylene diiso(thio)cyanates, bis(iso(thio)cyanatophenyl)methane and polyphenylpolymethylene polyiso(thio)cyanates, as prepared, for example, by aniline-formaldehyde condensation and subsequent phosgenation (MDI), propane diiso(thio)cyanates, butane diiso(thio)cyanates, pentane diiso(thio)cyanates, hexane diiso(thio)cyanates (e.g. hexamethylene diisocyanate, HDI), heptane diiso(thio)cyanates, octane diiso(thio)cyanates, nonane di- and triiso(thio)cyanates, decane di- and triiso(thio)cyanates, undecane di- and triiso(thio)cyanates, dodecane di- and triiso(thio)cyanates, isophorone diisocyanate (IPDI), bis(iso(thio)cyanatocyclohexyl)methane (e.g. $H_{12}$MDI, Desmodur®W), iso(thio)cyanatomethylmethylcyclohexane (e.g. 4(3)-iso(thio)

cyanatomethylcyclo-hexyl iso(thio)cyanate) themselves and the carbodiimides obtainable therefrom.

In the case of the isocyanates, the process by which they have been generated is unimportant, i.e. with or without use of phosgene.

Preference is given to using aliphatic isocyanates and mustard oils of the type mentioned above.

The 3-phospholenes used as starting materials and the preparation routes thereof are described in the literature: K. Dimroth in Comprehensive Heterocyclic Chemistry, Pergamon Press, Vol. 1, p. 514 ff, 1983 and literature cited therein.

The novel substances of the class of the 1,4,2-diazaphospholidines are crystalline solids or liquids and are found to be valuable products or intermediates for a series of applications, for example in catalysis. For instance, they are interesting catalysts for partial carbodiimide/uretonimine formation from isocyanates and for catalysis of the (partial) further reaction of the carbodiimide groups formed to 6-imino-1,3, 5-triazine-2,4-diones (iminotriazinediones, heterocycles formed from 2 mol of isocyanate and one mole of carbodiimide).

While the products of the formula (1) based on isocyanates or carbodiimides are generally colourless (provided that the parent isocyanate or carbodiimide does not bear a chromophore), the inventive conversion products of the isothiocyanates (mustard oils) are generally yellow to orange in colour.

They have reactivity typical of derivatives of trivalent phosphorus and can, for example, be oxidized by (atmospheric) oxygen or sulphur and alkylated on the phosphorus atom by alkylating agents.

Double bonds in the reactants are tolerated in the inventive reaction.

The inventive reaction can, especially in the aromatic series, also be conducted proceeding from isocyanates with intermediate formation of the carbodiimides—for example catalysed by small amounts of the P-oxides (1-organyl-2,5-dihydro-1H-phosphole 1-oxides, phospholene oxides) corresponding to the compounds of the formula (2), which may be present simultaneously in the reaction mixture—which generally affords mixtures of the compounds (1) where X=O and N—R2.

Since sterically demanding aliphatic isocyanates react significantly more slowly than linear aliphatic isocyanates, compounds with mixed substitution, for example of the formula (3), are also obtainable through suitable selection of the reaction conditions. The alkyl radical of the more reactive isocyanate occurs preferentially in the 4 position of the 1,4,2-diazaphospholidine-3,5-dione ring.

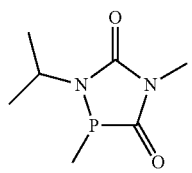

3

EXAMPLES

All feedstocks, unless stated otherwise, are products from Bayer or Lanxess.

Unless stated otherwise, operation was effected under strict exclusion of air under a dry nitrogen atmosphere.

The 1-organyl-2,5-dihydro-1H-phospholes (symmetric phospholenes) used were obtained by literature methods (cf. K. Dimroth in Comprehensive Heterocyclic Chemistry, Pergamon Press, Vol. 1, p. 514 ff, 1983 and literature cited therein).

$^1$H and $^{31}$P NMR spectroscopy analyses (the latter, unless stated otherwise, always proton-decoupled) were undertaken on in each case 10-15 mg of substance in 0.7 ml of dry, oxygen-free, CDCl$_3$-containing solutions on the DPX 400, AVC 400 or DRX 700 instruments from Bruker, Karlsruhe, Germany.

$^{13}$C NMR spectroscopy analyses were undertaken on approx. 30-50% samples in dry, oxygen-free CDCl$_3$ with the abovementioned instruments. The reference selected for the ppm scale was small amounts of tetramethylsilane in the appropriate solvent ($\delta$=0 ppm) or the solvent signal itself ($\delta$=77.0 ppm); a positive sign indicates shifting to a lower field relative to the standard.

The characteristic NMR data are reported as follows:

<Nucleus>NMR:<chem. shift [ppm]>(<multiplicity: s=singlet, d=doublet, t=triplet, q=quartet, m=multiplet>) <coupling constant [Hz]>.

The coupling nucleus is, unless stated otherwise, phosphorus.

Example 1

1,2,4-Trimethyl-1,4,2-diazaphospholidine-3,5-dione

To 1.4 g (24.5 mmol) of methyl isocyanate cooled to 0° C. were added dropwise, over the course of 10 min, 1.15 g (11.5 mmol) of 1-methyl-2,5-dihydro-1H-phosphole (symmetric 1-methylphosphole). The mixture was stirred for a further 4 h in a cold bath which gradually assumes room temperature, and then analysed. In addition to the signals of the target compound specified below, only very low-intensity signals of impurities were observed. The most intense among the latter is attributable to 1-methyl-2,5-dihydro-1H-phosphole 1-oxide (symmetric 1-methylphospholene oxide) ($^{31}$P: 65.3 ppm (s)).

The vacuum distillation of the reaction mixture afforded 1.75 g (95% of theory) of the target compound as a colourless, slightly oily liquid; b.p. 80° C./2 mbar.

$^{31}$P NMR: 30.7 ppm (s)

$^1$H NMR: 3.0 ppm (s); 2.9 ppm (d) 7.6 Hz; 1.4 ppm (d) 4.0 Hz, integration ratio 1:1:1

$^{13}$C NMR: 182.7 ppm (d) 2.9 Hz; 157.4 ppm (d) 5.8 Hz; 29.0 ppm (d) 16.5 Hz, 26.6 ppm (s), 15.5 ppm (d) 32.0 Hz The structure of the target compound was additionally confirmed by the results of high-resolution mass spectrometry: m/z=160.04041 (calc.: 160.04017) and the crystal structure analysis of the phosphorus sulphide (cf. Ex. 4).

Example 2

1,2,4-Trimethyl-1,4,2-diazaphospholidine-3,5-dithione

First, 320 mg (4.4 mmol) of methyl isothiocyanate (from ABCR) were melted (freed of dissolved gases) at bath temperature 45° C. under reduced pressure, supplied with nitrogen and then, after removing the external heat source, admixed dropwise with 200 mg (2 mmol) of 1-methyl-2,5-dihydro-1H-phosphole, in the course of which the colour deepened from yellow to orange. The orange mixture solidified rapidly, and was stirred at 70° C. for 4 h and then analysed. In addition to the signals of the target compound specified below, only very low-intensity signals of impurities were observed. The most intense of these was attributable to 1-methyl-2,5-dihydro-1H-phosphole 1-sulphide (symmetric 1-methylphospholene sulphide) ($^{31}$P: 55.3 ppm (s)).

The vacuum sublimation of the reaction mixture at 0.1 mbar/bath temperature 90° C. afforded 340 mg (88% of theory) of the target compound as an initially green-yellow fluorescent solid which had been converted to a lemon yellow crystal mass by the next day, m.p.: 75° C.

$^{31}$P NMR: 67.9 ppm (s)
$^1$H NMR: 3.7 ppm (s); 3.3 ppm (d) 6.5 Hz; 1.6 ppm (d) 5.0 Hz, integration ratio 1:1:1
$^{13}$C NMR: 215.4 ppm (d) 21.5 Hz; 184.9 ppm (d) 5.6 Hz; 36.2 ppm (s); 34.8 ppm (d) 15.6 Hz; 20.0 ppm (d) 35.9 Hz Example 3

1,4-Dibutyl-2-methyl-1,4,2-diazaphospholidine-3,5-dione a) To 8.85 g (89.2 mmol) of n-butyl isocyanate were rapidly added, at room temperature, 3.57 g (35.7 mmol) of 1-methyl-2,5-dihydro-1H-phosphole. In the course of this, the colourless liquid mixture warmed up only slightly and gradually changed colour to pale yellow. After stirring at room temperature for 16 h, analysis was effected by means of $^1$H and $^{31}$P NMR. In the $^{31}$P NMR spectrum, 3 singlets were observed at 65.1 ppm (1-methyl-2,5-dihydro-1H-phosphole 1-oxide), 24.1 ppm (target compound) and −41.0 ppm (1-methyl-2,5-dihydro-1H-phosphole, reactant) in an integration ratio of 1:17:35.7. In the $^1$H NMR spectrum, aside from the signals of the unconverted n-butyl isocyanate and of the abovementioned P-containing reactants and (by-)products, the 3 characteristic signal groups of 1,3-butadiene were detected (6.33-6.23 ppm (m); 5.20-5.11 ppm (m); 5.08-5.00 ppm (m); integration ratio 1:1:1). Signals for oligomers of n-butyl isocyanate were not discernible.

Subsequently, the mixture was stirred at 50° C. for a further 70 h and then worked up by distillation. This gave 7.4 g (85% of theory) of the target compound as a colourless, slightly oily liquid with b.p. 93° C./0.02 mbar.

$^{31}$P NMR: 24.2 ppm (s)
$^1$H NMR: approx. 3.4 ppm (m); 3.3 ppm (m); approx. 1.5 ppm (m), 1.4 ppm (d) 4.5 Hz; approx. 1.2 ppm (m); 0.82 ppm (t) $J_{HH}$ 7.05 Hz; 0.80 ppm (t) $J_{HH}$ 7.55 Hz, integration ratio 1:1:2:1.5:2:1.5:1.5
$^{13}$C NMR: 183.0 ppm (d) 1.9 Hz; 157.2 ppm (d) 5.8 Hz; 42.9 ppm (d) 14.6 Hz, 40.2 ppm (s), 31.6 ppm (d) 3.1 Hz; 30.0 ppm (s); 19.8 ppm (s); 19.7 ppm (s); 16.9 ppm (d) 32.9 Hz; 13.5 ppm (s)

The identity and purity (approx. 95%) of the target compound were additionally studied by means of high-resolution mass spectrometry: m/z=244.13479 (calc.: 244.13407). The most common secondary components were N,N'-di-n-butyl-carbodiimide (2.5%) and 1,3,5-tri-n-butyl-1,3,5-triazine-2,4,6-trione (tri-n-butyl isocyanurate, 1.4%).

b) To 0.97 g (9.8 mmol) of n-butyl isocyanate was added rapidly, at room temperature, 0.6 g (4.7 mmol) of 1,3,4-trimethyl-2,5-dihydro-1H-phosphole. No exothermicity was observed. The initially colourless, liquid mixture gradually changed in colour to pale yellow. After stirring at room temperature for 16 h, analysis was effected by means of $^1$H and $^{31}$P NMR. The conversion had advanced significantly further than in a); signals of by-products were not detected apart from the P-oxide (1,3,4-trimethyl-2,5-dihydro-1H-phosphole 1-oxide) and the 2,3-dihydro equivalents thereof (2 isomers) at 57.4 and 60.0/61.7 ppm (in total approx. 4% according to $^{31}$P NMR). The distillative workup afforded, in 95% yield, a significantly purer product (>99% according to GC) than in a) with the physical and spectroscopic data listed in a).

c) To 1.74 g (17.5 mmol) of n-butyl isocyanate was rapidly added, at room temperature, 0.8 g (7 mmol) of 1,3-dimethyl-2,5-dihydro-1H-phosphole. The colourless liquid mixture did not heat up and gradually changed in colour to pale yellow. After stirring at room temperature for 16 h, analysis was effected by means of $^1$H and $^{31}$P NMR. The conversion was between those observed under a) and b). Signals of by-products were not detected apart from the P-oxides (1,3-dimethyl-2,5(2,3)-dihydro-1H-phosphole-1-oxide, 66.4 (70.5) ppm, summary approx. 3.8 mol-% according to $^{31}$P NMR). The distillative workup afforded, in 94% yield, a product with purity comparable to b), with the physical and spectroscopic data listed in a).

Example 4

1,2,4-Trimethyl-1,4,2-diazaphospholidine-3,5-dione 2-sulphide

A mixture of 425 mg (2.6 mmol) of 1,2,4-trimethyl-1,4,2-diazaphospholidine-3,5-dione (cf. Ex. 1) with 157 mg (4.9 mmol) of elemental sulphur was heated to 70° C. for 24 h. Subsequently, the mixture was digested with a little methylene chloride, undissolved sulphur was filtered off and slow crystallization was induced by blanketing with n-hexane. A first crystal fraction (50 mg, 9.8% of theory, m.p. 95° C.) contained the single crystal studied by means of crystal structure analysis. The proposed structure was confirmed.

Example 5

1,4-Dibutyl-2,2-dimethyl-3,5-dioxo-1,4,2-diazaphospholidin-2-ium iodide

A mixture of 820 mg (3.3 mmol) of 1,4-dibutyl-2-methyl-1,4,2-diazaphospholidine-3,5-dione (cf. Ex. 3) with 6.27 g (44 mmol) of methyl iodide (from Aldrich) was heated at reflux (bath temperature: to 80° C.) while stirring with a magnetic stirrer bar for 24 h. The yellow mixture, whose viscosity had risen noticeably, was analysed by NMR spectroscopy without further workup:

$^{31}$P NMR: 39.2 ppm (95%), a by-product at 13.8 ppm (probably the P-oxide of the reactant, 5%)
$^1$H NMR: (only signals of the salt): approx. 4.0 ppm (m); approx. 3.7 ppm (m); 3.1 ppm (d) 14.6 Hz; approx. 1.7 ppm (m); approx. 1.6 ppm (m); approx. 1.4 ppm (m); approx. 1.3 ppm (m); 0.91 ppm (t) $J_{HH}$ 7.6 Hz; 0.89 ppm (t) $J_{HH}$ 7.55 Hz, integration ratio 1:1:3:1:1:1:1:1.5:1.5

Example 6

2,4-Dimethyl-1-(propan-2-yl)-1,4,2-diazaphospholidine-3,5-dione

To a mixture of 0.41 g (7.2 mmol) of methyl isocyanate and 6.13 g (72 mmol) of 2-propyl isocyanate was added, at room temperature, over the course of 1 h, 0.7 g (7 mmol) of 1-methyl-2,5-dihydro-1H-phosphole. No exothermicity was observed. The initially colourless liquid mixture gradually changed colour to pale yellow. Stirring at room temperature for 48 hours was followed by analysis by means of $^1$H and $^{31}$P NMR and GC-MS. As well as unconverted 1-methyl-2,5-dihydro-1H-phosphole and small amounts of the P-oxide thereof, essentially 2 singlets in the $^{31}$P NMR spectrum at 30.8 ppm (1,2,4-trimethyl-1,4,2-diazaphospholidine-3,5-dione; cf. Ex. 1) and 15.6 ppm (compound 3) were found. The integration ratio was 1:2.2. This ratio was determined by gas chromatography to be 1:3.5. The arrangement of the N-bonded exocyclic substituents was confirmed by means of 2D NMR.

Example 7

2-Methyl-1,4-di(prop-2-en-1-yl)-1,4,2-diazaphospholidine-3,5-dithione and 2-methyl-1,4-di(prop-2-en-1-yl)-1,4,2-diazaphospholidine-3,5-dithione 2-sulphide At room temperature, 1.15 g (11.6 mmol) of allyl isothiocyanate (from ABCR) were admixed dropwise with 56 mg (5.6 mmol) of 1-methyl-2,5-dihydro-1H-phosphole, in the course of which there was a clear deepening in colour from yellow to red-orange as the temperature increased slightly. After being left to stand overnight, the red-orange liquid mixture was analysed by means of $^{31}$P NMR: 64.3 ppm (s), and then converted to the P-sulphide with excess sulphur, 220 mg (6.99 mmol), $^{31}$P: 59.0 ppm (s), MS: molecular ion m/z 276 (70%), base peak: m/z 177, {M-allylNCS}.

Example 8

2-Methyl-1,4-diphenyl-1,4,2-diazaphospholidine-3,5-dione and N,N'-(2-methyl-1,4-diphenyl-1,4,2-diazaphospholidine-3,5-diylidene)dianiline To 2.8 g (23.5 mmol) of phenyl isocyanate was added dropwise, over the course of 10 min, 0.96 g (9.5 mmol) of 1-methyl-2,5-dihydro-1H-phosphole. In the course of this, the mixture warmed up slightly, changed colour to yellow-orange and solid deposition set in. After stirring/standing at room temperature for 24 hours, the mixture was dissolved in methylene chloride and analysed by means of $^{31}$P NMR and GC/MS.

$^{31}$P NMR: two singlets of about equal intensity at 38.3 and 34.5 ppm.

GC/MS: aside from traces of diphenylcarbodiimide, exclusively the target compounds (approx. 1:1) and 1,3,5-triphenyl-1,3,5-triazine-2,4,6-trione (triphenyl isocyanurate) and 1,3,5-triphenyl-6-(phenylimino)-1,3,5-triazine-2,4-dione (from 2 mol of phenyl isocyanate and one mole of diphenylcarbodiimide) were detected.

Example 9

Application Example for Catalysis

To 20.9 g (0.12 mol) of hexamethylene diisocyanate were added 1.7 g (7 mmol) of the compound described under Example 3b, and the mixture was stirred at 100° C. for 24 h. In the course of this, the refractive index ($n_D^{20}$) of the clear liquid mixture rose from 1.4559 to 1.4689. NMR spectroscopy proved the formation of uretonimine structures. Subsequently, addition of 920 mg of n-butanol stopped the reaction. Even in the course of further stirring at 100° C. (4 h), no further rise in the refractive index of the mixture was observed. The NMR spectrum remained unchanged.

The invention claimed is:

1. A 1,4,2-diazaphospholidine of the formula (1)

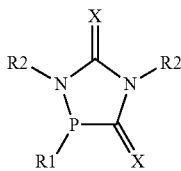

formula (1)

wherein
R1 represents $C_1$-$C_{20}$-alkyl,
R2 represent, each independently of one another, $C_1$-$C_{20}$-alkyl, -alkenyl groups with up to 20 C atoms, —or $C_5$-$C_{40}$-aryl groups, and
X represents identical or different substituents selected from the group consisting of O, S, and N—($C_5$-$C_{40}$-aryl).

2. The 1,4,2-Diazaphospholidine according to claim 1, wherein X is oxygen or sulphur.

3. A process for preparing a 1,4,2-diazaphospholidine of the formula (1)

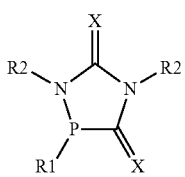

formula (1)

wherein
R1 represents $C_1$-$C_{20}$-alkyl,
R2 represent, each independently of one another, $C_1$-$C_{20}$-alkyl, alkenyl groups with up to 20 C atoms, —or $C_5$-$C_{40}$-aryl groups, and
X represents identical or different substituents selected from the group consisting of O, S, and N—($C_5$-$C_{40}$-aryl),
which comprises reacting a compound of the formula R2-NCX wherein R2 and X are as defined above with a 3-phospholene of the formula (2)

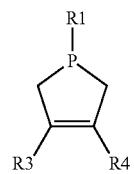

formula (2)

wherein
R1 is as defined above and
R3, R4 represent, independently of one another, a substituent selected from the group consisting of H, alkyl, and aryl.

4. The process according to claim 3, wherein R3, R4 represent, independently of one another, a hydrogen or a methyl group.

5. The process according to claim 3, wherein the 3-phospholene of the formula (2) is reacted with the compound of the formula R2-NCX in a molar ratio of 1:2 to 1:5.

6. The process according to claim 4, wherein the 3-phospholene of the formula (2) is reacted with the compound of the formula R2-NCX in a molar ratio of 1:2 to 1:5.

7. A catalyst comprising the 1,4,2-diazaphospholidines according to claim 1.

8. A catalyst comprising the 1,4,2-diazaphospholidines according to claim 2.

* * * * *